United States Patent [19]
Allen et al.

[11] Patent Number: 5,807,525
[45] Date of Patent: Sep. 15, 1998

[54] APPARATUS AND PROCESS FOR MULTI STAGE SOLID PHASE SYNTHESIS OF LONG CHAINED ORGANIC MOLECULES

[75] Inventors: Stephen Allen, Milford, Mass.; Hubert Köster, Hamburg, Germany; Edward Ashare, Framingham, Mass.; Donald W. Euwart, Natick, Mass.; Jennifer Fernandes, Milford, Mass.

[73] Assignee: Hybridon, Inc., Cambridge, Mass.

[21] Appl. No.: 608,702

[22] Filed: Feb. 29, 1996

Related U.S. Application Data

[60] Provisional application No. 60/010,165 Aug. 17, 1995.
[51] Int. Cl.⁶ ............................................ B23B 27/00
[52] U.S. Cl. .......................... 422/131; 422/134; 422/62; 422/82.05; 422/110; 935/88; 73/25.04; 73/29.01; 73/335.01
[58] Field of Search ................................ 422/131, 134, 422/62, 63, 67, 81, 82.05, 108, 110; 935/88; 73/25.04, 29.01, 335.01

[56] References Cited

U.S. PATENT DOCUMENTS 5,126,273  6/1992  Sheppard et al. ..................... 436/89
5,233,044  8/1993  Derek Hudson ...................... 548/110
5,466,608  11/1995  Lapluye et al. ....................... 436/86

FOREIGN PATENT DOCUMENTS 0 541 340 A2  5/1993  European Pat. Off. .
WO 92/15867  9/1992  WIPO .
WO 94/00471  1/1994  WIPO .
WO 94/01214  1/1994  WIPO .

OTHER PUBLICATIONS

Stewart, John M. et al., (1984), "Solid Phase Peptide Synthesis", *Pierce Chemical Company* (2nd ed.).

Letsinger, R.L., et al. (1965), "Oligonucleotide Synthesis on a Polymer Support", *Journal American Chemical Society*, 87, 3526–3527.

Agrawal, Sudhir (ed.) (1993), "Protocols for Oligonucleotide and Analogs: Synthesis and Properties", *Humana Press*, vol. 20 of Methods in Molecular Biology series.

*Primary Examiner*—Timothy McMahon
*Attorney, Agent, or Firm*—Lappin & Kusmer LLP

[57] ABSTRACT

An apparatus and process are disclosed for optimizing the repetitive steps in a solid-phase oligonucleotide synthesis by continuous optical scanning of the effluent stream from the reaction module and by computerized processing and implementation of the scanning data.

53 Claims, 2 Drawing Sheets

5,807,525

APPARATUS AND PROCESS FOR MULTI STAGE SOLID PHASE SYNTHESIS OF LONG CHAINED ORGANIC MOLECULES

This application claims the benefit of U.S. Provisional application Ser. No. 60/010,165 filed Aug. 17, 1995.

The present invention relates generally to improvements in the preparation of long-chained polymers (i.e. peptides, polysaccharides, nucleic acids, and the like), and more particularly to an improved apparatus and process for the solid-phase synthesis of oligonucleotides.

BACKGROUND OF THE INVENTION

Solid-phase, multi-stage synthesis of complex organic molecules using controlled fluid flow across a fixed bed is well-known in the art. This general technique has been successfully applied to the synthesis of peptides, oligonucleotides and similar long-chained organic substances. A good description of Merrifield's well-known work on solid-phase peptide synthesis appears in John M. Stewart and Janis D. Young's book "Solid Phase Peptide Synthesis" (2nd ed. 1984) published by Pierce Chemical Company, which book is incorporated herein by reference. A description of early work on solid-phase oligonucleotide synthesis appears in R. L. Letsinger and V. Mahadevan's article "Oligonucleotide Synthesis on a Polymer Support," in *Journal American Chemical Society*, vol. 87 at 3526–3527 (1965). A more recent and comprehensive discussion of the chemistry and synthesis techniques for oligonucleotide production appears in Sudhir Agrawal (ed.), "Protocols for Oligonucleotides and Analogs: Synthesis and Properties" (1993), published by Humana Press, Inc. as volume 20 of its "Methods in Molecular Biology" series, and this volume is also incorporated herein by reference.

Commercial-scale production of a growing variety of oligonucleotides has become increasingly important as these substances have moved out of the laboratory and into mainstream therapeutic applications. Thus, in one important commercial application, antisense oligonucleotide technology provides a novel approach to the inhibition of viral expression, and hence, to the treatment or prevention of various viral-associated diseases such as chronic and acute hepatitis, AIDS, hepatocellular carcinoma, and others. The oligonucleotides useful in such applications are typically composed of deoxyribonucleotides, ribonucleotides, modified oligonucleotides such as 2-O-methyl-ribonucleotides, or some combination thereof, generally comprising at least 6 nucleotides in length, preferably 12–50 nucleotides long, with 15 to 30mers being the most common. By binding to the complementary nucleic acid sequence, antisense oligonucleotides are able to inhibit splicing and translation of RNA, and transcription and replication of genomic DNA. In this way, antisense oligonucleotides are able to inhibit gene expression and protein translation.

The solid-phase synthesis of these complex organic molecules, illustrated schematically by the flow chart of FIG. 1, typically begins by fixing one end of a suitable starting molecule or precursor to an appropriate polymeric support. A typical precursor for oligonucleotide synthesis is an amidite, and a typical polymeric support comprises beads of controlled-pore glass (CPG) loaded with a suitably-protected nucleoside and contained in a column. Initially, the first building block (nucleoside) immobilized to the polymeric support is unreactive because of chemical blocking groups. Thus, the first reaction step of a synthesis operation is to deblock this first building block, typically accomplished by passing acid solution through the column containing the CPG beads and the precursor until the deblocking is substantially completed. The column must then be flushed with an appropriate washing liquid to remove any remaining acid and by-products formed during the deblocking reaction. Acetonitrile is commonly used as a wash in oligonucleotide synthesis.

When the wash step is substantially completed, the second reaction step, the coupling step, of the synthesis can begin. In the first coupling step, typically phosphoramidites are used as building blocks and are added to the free, reactive end of the first nucleoside anchored to the solid support using a suitable activator to promote the desired coupling reaction. Suitable activators include tetrazole in an acetonitrile solution. The amidite becomes relatively unstable once mixed with activator and must therefore be mixed just prior to addition to the reaction vessel. It will be appreciated that the failure to thoroughly flush acid and by-products from the system before beginning the coupling step could result in promoting undesired reactions which could adversely affect purity and yield as well as wasting relatively expensive raw materials. When the coupling reaction is substantially completed, the system must undergo another acetonitrile wash step to remove unreacted amidite and activator.

When this wash step is substantially completed, the third reaction step, an oxidation step, is initiated. In this step, oxygen, sulfur, or other oxidizing or sulfurizing reagent is introduced into the system to stabilize the newly-created phosphitetriester linkage. For example, an aqueous iodine solution may be utilized as an oxidant for the oxidation step of the process. When the oxidation step is substantially completed, still another acetonitrile wash step is used to remove any residual oxidant or solvent from the system in preparation for the fourth step of the synthesis. When this wash step is substantially completed, the final reaction step, the capping step, is started. In the capping step, materials such as acetic anhydride, N-methyl imidazole, and pyridine or mixtures thereof in predetermined ratios are added to the system to cap active sites at the free ends of incomplete nucleotide chains, i.e. chains that failed to complete the earlier coupling step. As with the activator and amidite solutions, the capping reagents are relatively unstable and must be mixed just prior to addition to the reaction chamber. This capping step is followed by still another wash step, after which the process returns to reaction step 1 to begin a new cycle for the addition of the next set of amidite molecules to the growing oligonucleotide chains.

This arduous and time-consuming multi-step cycle must be repeated each time the oligonucleotide chains are extended, twenty, thirty, forty times or more to produce the longer-chain oligonucleotides that have been found to have such important therapeutic applications. When the oligonucleotides have reached the desired lengths, a reagent such as ammonium hydroxide may be used to cleave the raw oligonucleotides from the polymeric support. The oligonucleotides thus obtained are separated, deprotected and purified by routine downstream processing to produce a final product.

In conventional laboratory solid-phase synthesis operations of the type described above, judgments as to when each reaction step and each washing step are substantially complete are typically based on a set of rough molar and thermodynamic calculations, or based on pre-established times, or some combination of both. Heretofore, there has been no apparatus or process for the precision monitoring of these reactions, and no way to optimize reaction/wash times or the quantities of reagents used. Opportunities for automating these arduous, expensive, and repetitive operations have been limited, and scaling-up these laboratory-sized syntheses for commercial production has proven expensive and difficult.

On the one hand, if any reaction step is not carried to substantial completion, ultimate yields of oligonucleotide product are adversely affected. On the other hand, permitting a reaction step to run too long wastes time and expensive raw materials (especially the amidites), leads to the formation of undesired by-products which must be separated and disposed of, and may in certain instances even lead to some deterioration of the growing nucleotide chains. Similarly, failure to optimize the timing of the various wash steps leads either to excessive impurities and product contamination if wash times are too short, or a loss of time and waste of material if wash times are too long. It will be appreciated that even a relatively small excess in a single wash step will lead to quite a large loss of time and waste of material when the wash step is repeated four times per cycle, and the cycle is repeated thirty or more times per batch of product. When a small laboratory synthesis is scaled-up to commercial-size production, for example to produce several grams or more of the desired product, small but recurrent deviations from optimum in any reaction or wash steps quickly grow into formidable and expensive obstacles.

These and other problems with and limitations of the prior art are overcome with the improved solid-phase oligonucleotide synthesis apparatus and process of this invention.

OBJECTIVES OF THE INVENTION

Accordingly, a principal object of this invention is to provide an apparatus and process for commercial (gram)-scale production of oligonucleotides.

It is a specific object of this invention to provide an apparatus and process for solid-phase synthesis of long-chained organic molecules wherein monitoring and feedback control are utilized to optimize the process parameters during various steps in the multi-stage operation.

It is also an object of this invention to automate and optimize a multi-step solid-phase synthesis of oligonucleotides by linking the electrical outputs of monitoring equipment to computerized implementation of system controls.

It is also an object of this invention to utilize multiple pumps and flowmeters to permit accurate ratio feed of multiple reagents to the reactor module.

Another object of this invention is to provide an integrated system for oligonucleotide synthesis in which fluid control valves are activated for initiating or terminating the feed of various reagents to a reaction chamber in predetermined sequence in feedback-controlled response to signals generated by monitoring equipment, such as optical scanners, located at one or more locations throughout the system to monitor the contents of associated fluid streams.

Specifically, it is an object of this invention to provide a feedback control system utilizing optical monitoring, such as an ultraviolet or visible light detector, to continuously monitor at least the fluid outlet stream from the reaction chamber in a solid-phase oligonucleotide synthesis in order to determine when each of the various reaction and wash steps in each chain-building cycle has gone substantially to completion.

Still other objects of this invention include providing various specifically-adapted components in an integrated, automated, optimized, commercial-scale oligonucleotide production operation designed to enhance product purity and yield.

Other objects and advantages of the present invention will in part be obvious and will in part appear hereinafter. The invention accordingly comprises the apparatus and process, involving the various components and the several steps, and the relation and order of one or more of such components or steps with respect to each of the others and to the apparatus, as exemplified in the following detailed disclosure and as illustrated by the drawings.

SUMMARY OF THE INVENTION

The oligonucleotide synthesis apparatus of this invention generally comprises a plurality of reagent reservoirs, each associated with a two- or three-way diaphragm valve, and interconnected by a system of inert fluid conduits to a reaction chamber containing a polymeric support and starting material for building a desired nucleotide chain. The apparatus comprises multiple pumps and flowmeters situated to combine otherwise unstable reagents in precise proportions directly before addition to the reaction chamber. The apparatus further comprises at least one monitoring device, such as an optical scanner, located to continuously monitor the chemical composition of the outlet fluid from the reaction chamber thereby to determine when each of the various reaction and wash steps are substantially completed. Signals from the monitoring device are fed to an associated computer system programmed to automatically open or close various valves in response to those signals, thus controlling the timing and sequence of flow of the various reagents in the several reservoirs to the reaction chamber. In its principal embodiment, the process of this invention comprises feedback control of an integrated oligonucleotide synthesis by detecting and monitoring the compositions of feed streams and/or effluent streams during both reaction and wash cycles. Optimization of process parameters is thereby achieved facilitating commercial-scale production of the valuable oligonucleotide products.

DETAILED DESCRIPTION OF PREFERRED EMBODIMENTS

Figure 1:
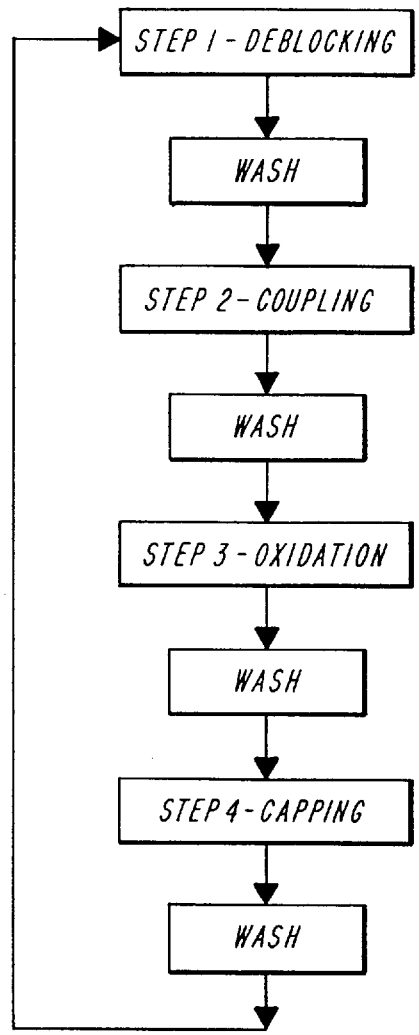
FIG. 1 is a process flow chart illustrating a typical single cycle in building a nucleotide chain.
Figure 2:
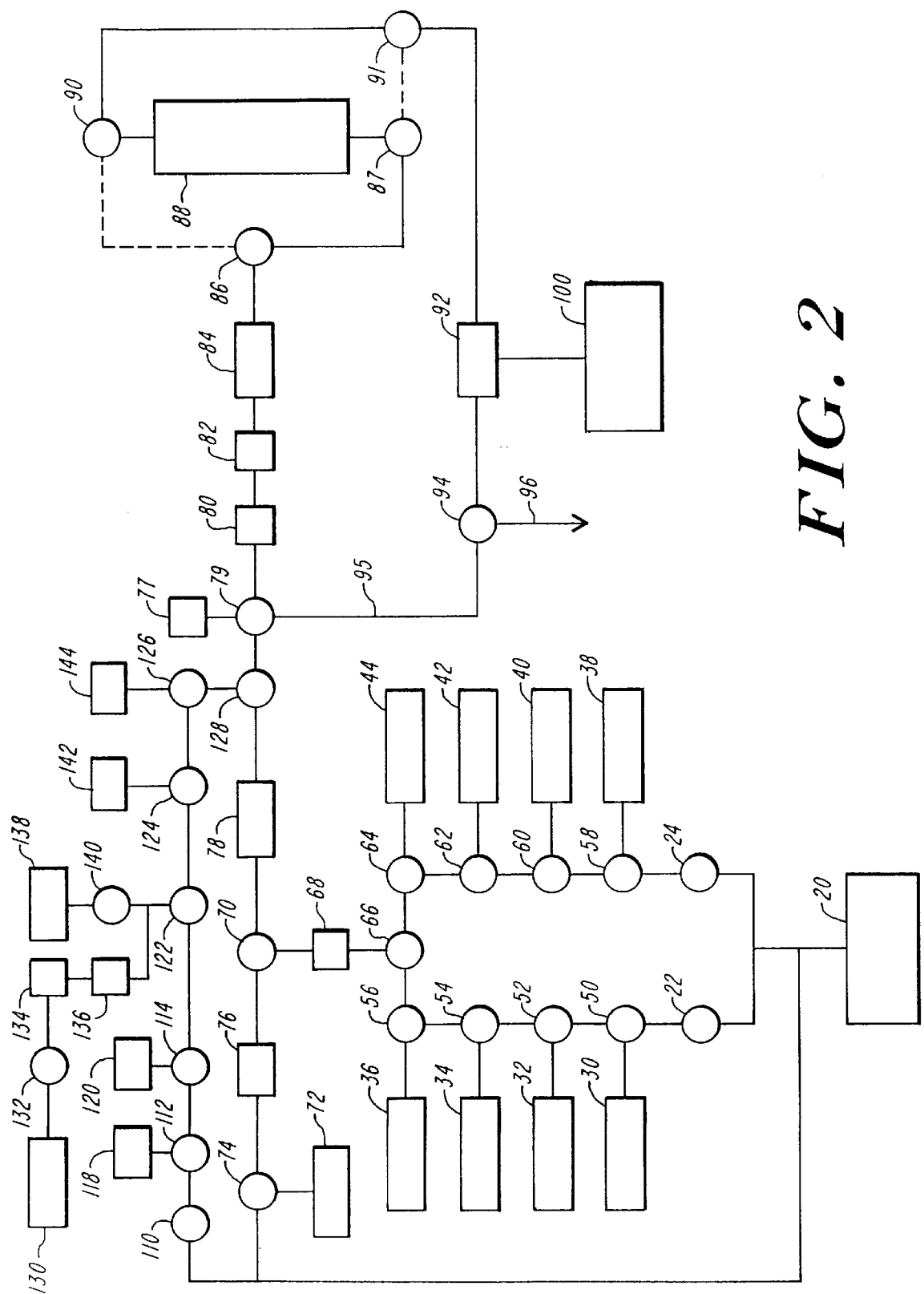
FIG. 2 is a schematic illustration of one representative embodiment of the overall oligonucleotide production system of this invention.

In accordance with one embodiment of this invention, the multi-step nucleotide chain-building synthesis, as generally illustrated in FIG. 1, can be scaled-up for commercial production designed to produce several grams or more of product utilizing an optimized, automated system as shown in FIG. 2. It will be understood by those skilled in the art that the exact sequence of steps as illustrated in FIG. 1 may vary depending on the recipe being used to synthesize a particular end product. Thus, in some applications, step 4 (capping) might come before step 3 (oxidation), and so forth. In FIG. 2, reaction vessel 88 is first loaded with a suitable starting material, such as a protected nucleoside or other building blocks, fixed at one end of the chain to a suitable polymeric support such as CPG beads. Reaction vessel 88 is then connected to a set of reagent reservoirs by an interconnected system of fluid conduits (not numbered) that are made of a material that is substantially inert with respect to all of the various reagents used in the process. Thus, tubing for use in this system may be advantageously fashioned from a fluorocarbon polymer plastic or high-quality stainless steel.

Perfluoroalkane (PFA) tubing is especially preferred in this application because it is readily available commercially and combines a high level of inertness with somewhat better resilience than a tetrafluoroethylene resin like Teflon.

In reaction step 1 (see FIG. 1) of a chain-building cycle, a flowstream of a suitable deblocking compound, such as a solution of dichloro acetic acid (DCA) in methylene chloride, is withdrawn from fluid reservoir 144 through three-way valves 126 and 128 and routed through the fluid conduit containing pump 80, flowmeter 82, and one or more valves, such as three-way valves 86 and 87, to the bottom of reaction vessel 88. The deblocking solution is then passed upward through vessel 88 contacting the protected nucleoside or oligonucleotide fixed to the CPG beads resulting in unblocking or activating those functional groups. A flowstream comprising reaction by-products and excess deblocking solution is withdrawn as effluent from the top of vessel 88, passed through one or more control valves, such as three-way valves 90 and 91, and directed through or past a monitoring device, such as optical scanner 92, which continuously monitors the chemical composition of the flowstream exiting vessel 88.

Optical scanner 92 preferably comprises an ultraviolet (UV) or visible light detector capable of monitoring at least two wavelengths. Such scanners are well-known in the art and relatively inexpensive. Still better, although somewhat more expensive, are full spectrum UV/visible scanners, which are also well-known and commercially available. Other types of optical scanners, such as infrared (IR) scanners, are also considered to be within the scope of this invention. For optical scanner 92 to operate, of course, the portion of the outlet fluid conduit to which it is adjacent must contain an optically transparent window, such as a quartz window, to permit relatively unimpeded and undistorted entry and exit of the UV or other light used for monitoring. In addition, as they become more reliable and cost-effective, it is anticipated that other monitoring devices, for example density monitors, could be substituted for or used in conjunction with one or more of the optical scanners used herein.

Either based on calibration or calculation, optical scanner 92 can be used to determine when the deblocking step has been substantially completed and the flow of deblocking solution through vessel 88 should therefore be discontinued. In a particularly preferred embodiment, electrical signals from optical scanner 92 can be fed to a computer unit 100 programmed to evaluate the incoming signals, to determine from the scanning data the substantial completion of the deblocking (or any other) step, and to effectuate the transition from one process step to the next by electronically closing one set of system valves and opening another.

This computerized embodiment of the invention represents a highly automated, highly optimized, and extremely efficient oligonucleotide synthesis that can process vastly larger quantities of product in much shorter times than anything that has ever before been achieved. For example, whereas conventional oligonucleotide synthesis equipment and processes have a maximum realizable output of about 3 millimoles (typically a fraction of a gram) of product over about a twenty hour period, the computerized embodiment of this invention has an expected output of at least about 100 millimoles (typically several grams) of the same product over about a twelve hour period. This dramatic and wholly unexpected improvement in production turns an essentially small-scale laboratory process into a viable commercial enterprise.

During at least some of the process steps, it may be desirable to recycle some portion of the reactor effluent as recycle stream 95 coming out of three-way valve 94, mixing stream 95 with fresh reagent at three-way valve 79, while withdrawing another portion of the effluent as waste stream 96 for disposal. For example, during the deblocking step, the effluent from reaction vessel 88 will contain unreacted DCA, a portion of which can be usefully recycled. During a wash step, however, recycling would simply return contaminants to the reaction environment and, thus, should generally be avoided.

Upon completion of the deblocking step, valve 126 is closed to stop the flow of deblocking solution from reservoir 144. Instead, two-way valve 110 and three-way valves 112, 114, 122, 124, 126 and 128 are positioned to permit the flow of washing fluid, typically acetonitrile, from wash reservoir 20 through the connecting fluid passage to the bottom of vessel 88. Along the way to vessel 88, the wash fluid would flush the fluid passageway of residual deblocking solution. As the wash fluid passes through the interior of vessel 88, it also picks up residual deblocking solution and by-products of the deblocking reaction. Exiting the top of vessel 88, the effluent wash stream passes scanner 92, where it is continuously monitored, and is withdrawn at valve 94 as waste stream 96. Similar to the deblocking step, optical or other monitoring of the effluent wash stream can be used to determine relatively precisely when the wash step has been substantially completed. Also similar to the deblocking step, signals from the optical scanner can be relayed to computer 100, which is programmed to automatically switch the system from the wash step to the next reaction step when the wash step is substantially completed.

Upon completion of this wash step, it is time to begin reaction step 2 of the cycle, the coupling step. Valves 110 and 128 are closed to stop the flow of acetonitrile wash fluid, and, instead, valves associated with one of the several amidite reservoirs are opened. Reservoirs 30, 32, 34, 36, 38, 40, 42 and 44 hold eight different amidites which can be used in the synthesis of a desired oligonucleotide. It will be apparent to those skilled in the art that fewer or greater numbers of amidite reservoirs may be utilized in this system as required for a particular synthesis. As shown in FIG. 2, each amidite reservoir has associated therewith a three-way valve, namely valves 50, 52, 54, 56, 58, 60, 62 and 64 respectively. The apparatus as shown in FIG. 2 may be utilized for the synthesis of a nucleotide chain having fewer than eight different amidite components by simply leaving the extra reservoirs empty and the associated valves closed and deactivated. By selectively activating and opening one of the valves 50, 52, etc., amidite can be withdrawn from any one of the amidite reservoirs and directed through three-way valve 66 and flowmeter 68 on the way to reaction vessel 88, while the other seven valves remain closed and their associated amidite reservoirs stay off-line.

Activator compound is stored in reservoir 72 and is also fed into the system during the coupling reaction step (step 2) via three-way valve 74 and pump 76. A preferred activator for oligonucleotide synthesis is a solution of tetrazole in acetonitrile. Due to the instability of the amidite/activator solution, the reagents are ratio fed to the reaction vessel 88 in order to maintain optimum proportions of the reagents. The flow meters 68 and 82 monitor the different stream flowrates. These flowrates are utilized by the process controller to adjust the pumps 80 and 76 to provide activator and amidite through the three-way mixing valve 70 to the reaction chamber 88 in the optimum predetermined proportions. In one embodiment of the invention as shown in FIG. 2, another monitoring device, such as optical scanner 78, may be located along the flow path between valves 70 and 128 and used to confirm the identity of the amidite being added. In an alternative embodiment of the invention as shown in FIG. 2, a third monitoring device, such as optical scanner 84, may be located along the flow path between flowmeter 82 and three-way valve 86 to monitor the composition of the feed stream to vessel 88, for example following the addition of a recycle stream 95 of effluent from vessel 88. Whereas monitoring device 92 is an indispensable element of this invention, however, the use of additional monitoring devices, such as scanners 78 and 84, at other locations in the system is optional and not required for the operability of the invention.

As described above in connection with the deblocking step and the following wash step, during the coupling step effluent from reactor vessel 88 is passed through scanner 92, where it is continuously monitored to determine when the coupling reaction is substantially completed. Signals from scanner 92 may again be relayed to computer unit 100 for automatically switching the system to the next wash step when the coupling step is completed. At this point, the valve 50, 52 etc. associated with the amidite reservoir would be closed, as would valve 74 associated with the activator reservoir. Two-way valves 22 or 24 would be positioned, along with the other valves in the respective amidite fluid line, to facilitate flushing that line with wash fluid from reservoir 20. Also valves in the line containing valves 74, 70 and 128 would be positioned to permit the flow of wash fluid through this line to flush out residual activator. The wash fluid would also eventually be channeled through vessel 88 to flush out activator, unreacted amidite, and coupling reaction by-products. As before, the effluent stream from vessel 88 during this second wash step would pass through optical scanner 92 for continuous monitoring to determine substantial completion of this wash step and, preferably, with computer-actuated valve switching at the proper time based on the scanner output.

Upon completion of this second wash step, it is time to begin reaction step 3 of the cycle, the oxidation step. Valves are closed to stop the flow of wash fluid, and, instead, three-way valves 124, 126 and 128 are opened to begin the flow of oxidizing or sulfurizing solution from oxidation reservoir 142 to vessel 88. As before, during this oxidation step effluent from reactor vessel 88 is passed through scanner 92, where it is continuously monitored to determine when the oxidation reaction is substantially completed. Signals from scanner 92 can be relayed to computer unit 100 for automatically switching the system to the next wash step when the oxidation step is completed. During the oxidation step, some portion of the effluent stream from vessel 88, containing unreacted oxidant, may be advantageously recycled to vessel 88 via recycle stream 95.

When the oxidation reaction is substantially completed, valve 124 is closed to stop the flow of oxidant from reservoir 142. Valves 110, 112, 114, 122, 124, 126 and 128 are positioned, however, to permit wash fluid from reservoir 20 to flush the line that had carried the oxidation solution, as well as to flush residual oxidation solution and by-products from the oxidation reaction from vessel 88. As before, the effluent stream from vessel 88 during this third wash step passes through scanner 92 for continuous monitoring to determine substantial completion of this wash step, preferably with computer-actuated valve switching at the appropriate time based on the scanner output.

Upon completion of this third wash step, it is time to begin reaction step 4 of the cycle, the capping step. Valves are closed to stop the flow of wash fluid, and, instead, two-way valves 132 and/or 140, together with valves 122, 124, 126 and 128, are positioned to begin the flow of capping compound to vessel 88. In a preferred embodiment as shown in FIG. 2, a ratioed mixture of two different capping compounds may be utilized in this step. As illustrated, reservoir 130 contains a first capping material, such as acetic anhydride, while reservoir 138 contains a second capping material, such as a base N-methyl imidazole. An optimum mass ratio of the two capping materials being fed to vessel 88 may be calculated or determined by routine experimentation, and that optimum ratio can then be established and maintained using pump 134 and flowmeter 136 to control the mass flow of material from reservoir 130. During this capping step, effluent from reactor vessel 88 is passed through scanner 92, where it is continuously monitored to determine when the capping reaction is substantially completed. Signals from scanner 92 can be relayed to computer unit 100 for automatically switching the system to the next wash step when the capping step is completed. During the capping step, some portion of the effluent stream from vessel 88, containing unreacted capping compounds, may be advantageously recycled to vessel 88 via recycle stream 95.

When the capping reaction is substantially completed, valves 132 and 140 are closed to stop the flow of capping materials from reservoirs 130 and 138 respectively. Valves 110, 112, 114, 122, 124, 126 and 128 are positioned, however, to permit wash fluid from reservoir 20 to flush the line that carried the capping fluid mixture, as well as to flush residual capping materials and by-products from the capping reactions from vessel 88. The effluent stream from vessel 88 during this fourth wash step passes through scanner 92 for continuous monitoring to determine substantial completion of this final wash step, preferably with computer-actuated valve switching at the appropriate time based on the scanner output.

Upon completion of this fourth and final wash step, a single complete chain-building cycle is completed. At this point, the system illustrated in FIG. 2 cycles back to begin a new chain-building addition, as shown schematically in FIG. 1, and repeat the four reaction steps and four wash steps as described above. The system of FIG. 2 repeats this cycle until the chains in vessel 88 reach the desired length to form the desired oligonucleotide product. At this point, following the last wash step, valve 114 can be opened to begin the flow of the cleavage compound, typically ammonium hydroxide, from reservoir 120 through the system to vessel 88. The effect of the cleavage compound is to separate the completed nucleotide chains from the CPG polymer support in vessel 88. The effluent from vessel 88 in this step of the process contains the raw oligonucleotide product, which is recovered by conventional means for further deprotection and purification. In this step of the process, scanner 92 may be utilized to determine when the cleavage reaction is substantially completed and all of the oligonucleotide product recovered from vessel 88.

Although the apparatus and synthesis process as described above represent the heart of this invention, in the preferred practice of the invention a variety of apparatus and/or process variations or enhancements may contribute to improved yields and a higher purity product. As previously discussed, in this multi-step synthesis operation, cleanliness of the system in between the various reaction steps is essential to prevent an accumulation of contaminants from earlier steps interfering with later steps. In this connection, two- and three-way diaphragm-type fluid valves having interior surfaces made of inert material, such as a fluorocarbon plastic polymer or high-quality stainless steel, when utilized throughout the system, have been found to yield surprisingly superior results compared to other conventional valve constructions. The diaphragm-type valves minimize wetted interior surfaces subject to fluid corrosion as well as providing an interior configuration which facilitates complete sweeping with the wash fluid during the wash steps. Diaphragm-type valves suitable for use in this invention, which may be operated automatically in response to computer-generated electrical signals, are known in the art and available commercially.

Another useful enhancement of the basic apparatus and process of this invention is the use of one or more flowmeters in the fluid conduits, for example flowmeter 82, which is capable of monitoring fluid density as well as measuring and regulating mass flowrates. In a fully automated, computer-driven system as shown in FIG. 2, fluid density measures at one or more points in the system over time can be useful in monitoring the on-going process and in providing data for making mid-course adjustments as necessary. Such density monitoring can supplement or, in some cases, substitute for one or more of the optical scanners.

In a preferred embodiment of the invention, means are also provided for monitoring the moisture content of any feed streams entering reaction vessel 88. Because the presence of water can adversely affect one or more of the various reactions being carried out in vessel 88, particularly the coupling and capping steps, it is normally desirable to maintain low or substantially zero tolerance for moisture. For example, a moisture monitoring device 77 located at valve 79, where recycle stream 95 is mixed with a fresh reagent stream from valve 128, can monitor moisture levels in both the fresh reagent and the recycle stream. Signals from moisture monitor 77 can be relayed to computer unit 100 for automatically controlling valves 79 and 94. Thus, if the moisture level in the fresh reagent stream should reach an unacceptably high level at any time during the synthesis, valves 79 and 94 can be automatically switched so as to divert the reagent stream to waste stream 96 and thereby prevent contamination of the contents of column 88.

In another alternative embodiment of this invention, fluid conduits leading to and from reaction vessel 88 can be arranged to facilitate reverse (downward) flow through the column. Thus, by appropriately switching valves 86, 87, 90 and 91, fluid flow can be directed from valve 86 to valve 90 (as shown by the dotted lines), then into the top of column 88. The effluent stream is withdrawn from the bottom of column 88, and directed from valve 87 to valve 91 (as shown by the dotted lines), where it rejoins the main fluid conduit system. Reverse flow through column 88 may be utilized periodically to optimize distribution in the reactor and to complete utilization of all reactive sites in the bed.

Still another useful enhancement in the apparatus and process of this invention is the use of a Triplex pump, for example pump 80 in FIG. 2. The advantages of the Triplex pump used for pump 80 are that it has a wide range of fluid flow capabilities and pressures, and the smooth pumping action of this design helps to avoid unduly disturbing the bed of reaction vessel 88. Such pumps are known in the art and available commercially.

For some applications, it may be useful to design the system with a spare fluid reservoir and associated three-way valve, as shown at 118 and 112 respectively in FIG. 2. This configuration permits ready adaptation of the system to accommodate an additional reagent. Also, in place of a single reaction vessel 88, it is within the scope of this invention to utilize two or more reaction vessels placed on line in parallel configuration. Two or more side-by-side reaction vessels could be run simultaneously or, alternatively, sequentially in a semi-continuous batch processing mode. It will be apparent that simultaneous operation of two or more reaction vessels would necessitate a separate optical scanner associated with each reactor effluent stream. It will also be apparent that a multiple reaction chamber configuration would necessitate corresponding changes in the configuration of valves and fluid conduits leading to and away from the multiple reactors. Such routine adaptations can be effected by those of ordinary skill in the art.

Programmable logic-controlling (PLC) computer units capable of receiving continuous electrical inputs from an optical scanner, as well as data on valve positions, flowrates, densities, pressures, etc., and processing that data according to certain predetermined algorithms, and generating electrical outputs based on that data for selectively activating one or more valves in a system such as that shown in FIG. 2, are well-known in the art. Programming the computer software to carry out the monitoring, optimizing, feedback control, and automation functions as described herein is within the purview of those of ordinary skill in this art. Software will utilize custom-tailored recipes for each particular oligonucleotide synthesis depending on the particular reagents used and other desired process parameters.

Although this description has focussed on the multi-stage solid-phase synthesis of oligonucleotides, it will be apparent to those skilled in the art that the apparatus and process of this invention have application to the synthesis of other long-chained organic molecules, for example, peptides, polysaccharides, and both RNA- and DNA-based oligomers and analogs thereof such as peptide nucleic acids (PNA) and other mimetics, and may be adapted to such related applications based on routine experimentation. All of such related applications are also considered to be within the scope of this invention.

The present invention thus represents a dramatic and unexpected improvement over prior art systems in oligonucleotide synthesis. This invention leads to optimization of reaction and wash times, as well as optimization of the quantities of reagents. This invention makes possible economical, commercial-scale production of these increasingly valuable and important complex organic materials. This invention also leads to optimum yields of a purer product, at lower cost, and in less time than has heretofore been possible.

Equivalents

Since certain changes may be made in the above-described apparatus and process without departing from the scope of the invention herein involved, it is intended that all matter contained in the above description shall be interpreted in an illustrative and not in a limiting sense. Thus, those skilled in the art will recognize, or be able to ascertain, using no more than routine experimentation, numerous equivalents to the specific substances and procedures described herein. Such equivalents are considered to be within the scope of this invention, and are covered by the following claims.

Having described the invention, what we claim is:

1. An apparatus for the multi-stage solid-phase synthesis of long-chained organic compounds, said apparatus comprising in combination: (a) chamber means suitable for containing a support material and attached building blocks; (b) a plurality of fluid reservoirs; (c) conduit means interconnecting each of said fluid reservoirs with said chamber means; (d) valve means associated respectively with each of said fluid reservoirs; (e) in-line pump means for promoting mixing of two or more reagents and for fluid flow through said conduit means for provide a feedstream to said chamber means; and (f) first detection and monitoring means comprising first optical scanning means capable of monitoring ultraviolet or visible light of at least two wavelengths for continuously monitoring the chemical composition of effluent from said chamber means.

2. An apparatus according to claim 1 further comprising means for detecting and monitoring the moisture content of said feedstream to said chamber means.

3. An apparatus according to claim 1 further comprising a feedback control system for receiving signals from said first detection and monitoring means and for activating one or more of said valve means in response to said signals.

4. An apparatus according to claim 3 wherein said feedback control system comprises a programmable logic-controlling computer unit.

5. An apparatus according to claim 1 wherein at least one of said fluid reservoirs comprises a wash fluid reservoir positioned along said conduit means such that every portion of any conduit means that might carry two or more different reagents between said fluid reservoirs and said chamber means can be swept by wash fluid from said wash fluid reservoir.

6. An apparatus according to claim 1 further comprising at least a flowmeter to monitor fluid flow in said conduit means.

7. An apparatus according to claim 6 wherein said flowmeter also measures fluid density.

8. An apparatus according to claim 7 further comprising a feedback control system for receiving signals from said flowmeter and for activating one or more of said valve means in response to said signals.

9. An apparatus according to claim 8 wherein said feedback control system comprises a programmable logic-controlling computer unit.

10. An apparatus according to claim 1 further comprising at least a second detection and monitoring means positioned along a portion of said conduit means different from that of said first detection and monitoring means for monitoring the chemical composition of the flowstream in said different portion of said conduit means.

11. An apparatus according to claim 10 wherein said second detection and monitoring means comprises a second optical scanner.

12. An apparatus according to claim 11 wherein said second optical scanner is capable of monitoring ultraviolet or visible light of at least two wavelengths.

13. An apparatus according to claim 1 wherein said conduit means comprises a fluorocarbon polymer plastic.

14. An apparatus according to claim 1 wherein said conduit means comprises perfluoroalkane tubing.

15. An apparatus according to claim 1 wherein said conduit means comprises stainless steel.

16. An apparatus according to claim 1 further comprising an optically transparent window in the side of said conduit means adjacent said first scanning means.

17. An apparatus according to claim 16 wherein said window is made of quartz.

18. An apparatus according to claim 1 wherein at least some of said valve means comprise diaphragm valves.

19. An apparatus according to claim 1 wherein all of said valve means are diaphragm valves.

20. An apparatus according to claim 1 comprising at least seven fluid reservoirs.

21. A system for the synthesis of oligonucleotides comprising: (A) a reaction vessel having fluid inlet and outlet means and loaded with a support material having one end of a nucleotide chain attached thereto; (B) a plurality of fluid reservoirs including (a) a wash fluid reservoir for containing a wash fluid, (b) at least two amidite reservoirs for containing different amidite compounds, (c) a deblocking reservoir for containing a deblocking compounds, (d) an activator reservoir for containing an activator, (e) an oxidant reservoir for containing an oxidant, (f) at least a capping reservoir for containing a capping compound, and (g) a cleaving reservoir for containing a cleaving compound; (C) an interconnected set of fluid passageways connecting each of said reservoirs to said reaction vessel; (D) at least a valve associated with each said fluid reservoir for regulating fluid flow from the respective reservoir into said passageways; (E) at least a pump for generating fluid flow and promoting mixing of two or more reagents and at least a flowmeter for monitoring fluid flow through at least one of said passageways; (F) first optical scanning means capable of monitoring ultraviolet or visible light of at least two wavelengths adjacent said reaction vessel fluid outlet means; and (G) a computer processing unit in electrical communication with said first optical scanning means and each of said valves.

22. A system according to claim 21 wherein said support material comprises controlled-pore glass beads.

23. A system according to claim 21 further comprising moisture detection means for detecting and monitoring the water content of the fluid in said reaction vessel fluid inlet means.

24. A system according to claim 23 further wherein said moisture detection means is in electrical communication with said computer processing unit.

25. A system according to claim 21 wherein said oxidant is selected from the group consisting of oxidizing compounds and sulfurizing compounds.

26. A system according to claim 21 wherein said oxidant is an aqueous iodine solution.

27. A system according to claim 21 wherein wash fluid from said wash fluid reservoir can sweep every portion of those fluid passageways that, at different times, carry reagents from two or more of said reservoirs.

28. A system for the synthesis of oligonucleotide analogs comprising: (A) a reaction vessel having fluid inlet and outlet means and loaded with a support material having one end of a nucleotide analog attached thereto; (B) a plurality of fluid reservoirs including (a) a wash fluid reservoir for containing a wash fluid, (b) at least two building block reservoirs for containing different building block compounds, (c) a deblocking reservoir for containing a deblocking compound, (d) an activator reservoir for containing an activator, (e) at least a capping reservoir for containing a capping compound, and (f) a cleaving reservoir for containing a cleaving compound; (C) an interconnected set of fluid passageways connecting each of said reservoirs to said reaction vessel; (D) at least a valve associated with each said fluid reservoir for regulating fluid flow from the respective reservoir into said passageways; (E) at least an in-line pump for generating fluid flow and promoting mixing of two or more reagents and at least a flowmeter for monitoring fluid flow through at least one of said passageways; (F) first optical scanning means adjacent said reaction vessel fluid outlet means, said first optical scanning means being capable of monitoring ultra violet or visible light of at least two wavelengths; and (G) a computer processing unit in electrical communication with said with said first optical scanning means and each of said valves.

29. A system according to claim 28 comprising at least first and second in-line pumps located respectively in first and second passageways, said first and second passageways being separated by at least an intermediate valve.

30. A system according to claim 29 further comprising first and second flowmeters, one being located upstream of said intermediate valve, the other being located downstream of said intermediate valve.

31. An apparatus for the multi-stage solid-phase synthesis of long-chained organic compounds, said apparatus comprising in combination: (a) at least a reaction chamber suitable for containing a support material and attached building blocks; (b) a plurality of fluid reservoirs, at least one of which is a wash fluid reservoir containing wash fluid and at least two of which are reagent reservoirs containing different reagents; (c) conduit means interconnecting each of said fluid reservoirs with said reaction chamber wherein said wash fluid reservoir is positioned along said conduit means such that every portion of any conduit means that might carry two or more different reagents between said reagent reservoirs and said chamber means can be swept by wash fluid from said wash fluid reservoir; (d) valve means associated respectively with each of said fluid reservoirs; (e) pump means positioned in said conduit means so as to promote mixing of two or more reagents and for generating fluid flow through said conduit means to provide a feedstream to said reaction chamber; and (f) first detection and monitoring means comprising first optical scanning means being capable of monitoring ultra violet or visible light of at least two wavelengths for continuously monitoring the chemical composition of effluent from said reaction chamber.

32. An apparatus according to claim 31 further comprising means for detecting and monitoring the moisture content of said feedstream to said chamber means.

33. An apparatus according to claim 31 further comprising a feedback control system for receiving signals from said first detection and monitoring means and for activating one or more of said valve means in response to said signals.

34. An apparatus according to claim 33 wherein said feedback control system comprises a programmable logic-controlling computer unit.

35. An apparatus according to claim 31 further comprising at least a flowmeter to monitor fluid flow in said conduit means.

36. An apparatus according to claim 35 wherein said flowmeter also measures fluid density.

37. An apparatus according to claim 36 further comprising a feedback control system for receiving signals from the said flowmeter and for activating one or more of said valve means in response to said signals.

38. An apparatus according to claim 37 wherein said feedback control system comprises a programmable logic-controlling computer unit.

39. An apparatus according to claim 31 further comprising at least a second detection and monitoring means positioned along a portion of said conduit means different from that of said first detection and monitoring means for monitoring the chemical composition of the flowstream in said different portion of said conduit means.

40. An apparatus according to claim 39 wherein said second detection and monitoring means comprises a second optical scanner.

41. An apparatus according to claim 40 wherein said second optical scanner is capable of monitoring ultraviolet or visible light of at least two wavelengths.

42. An apparatus according to claim 31 further comprising an optically transparent window in the side of said conduit means adjacent said first scanning means.

43. An apparatus according to claim 42 wherein said window is made of quartz.

44. An apparatus according to claim 31 wherein at least some of said valve means comprise diaphragm valves.

45. An apparatus according to claim 31 wherein all of said valve means are diaphragm valves.

46. An apparatus according to claim 31 comprising at least seven fluid reservoirs.

47. An apparatus according to claim 31 further wherein each of said reagent reservoirs is connected to the portion of said conduit means going to said reaction chamber at a point intermediate between where the portion of said conduit means connects to said reaction chamber and where it connects to said wash fluid reservoir.

48. A system for the synthesis of oligonucleotide analogs comprising: (A) at least a reaction vessel having fluid inlet and outlet means and loaded with a support material having one end of a nucleotide analog attached thereto; (B) a plurality of fluid reservoirs including (a) a wash fluid reservoir for containing a wash fluid, (b) at least two building block reservoirs for containing different building block compounds, (c) a deblocking reservoir for containing a deblocking compound, (d) an activator reservoir for containing an activator, (e) at least a capping reservoir for containing a capping compound, and (f) a cleaving reservoir for containing a cleaving compound, (C) an interconnected set of fluid passageways connecting each of said reservoirs to said reaction vessel, further wherein each of said building block reservoirs, deblocking reservoirs, activator reservoirs, capping reservoirs, and cleaving reservoirs is connected to the portion of said fluid passageways going to said reaction vessel at a point intermediate between where the portion of said fluid passageways connects to said reaction vessel and where it connects to said wash fluid reservoir; (D) at least a valve associated with each said fluid reservoir for regulating fluid flow from the respective reservoir into said passageways; (E) at least a pump for generating fluid flow and positioned in said fluid passageways so as to promote mixing of two or more reagents and at least a flowmeter for monitoring fluid flow through said passageways;(F) first optical scanning means being capable of monitoring ultraviolet or visible light of at least two wavelengths adjacent said reaction vessel fluid outlet means; and (G) a computer processing unit in electrical communication with said first optical scanning means and each of said valves.

49. A system according to claim 48 wherein said support material comprises controlled-pore glass beads.

50. A system according to claim 48 further comprising moisture detection means for detecting and monitoring the water content of the fluid in said reaction vessel fluid inlet means.

51. A system according to claim 50 further wherein said moisture detection means is in electrical communication with said computer processing unit.

52. A system according to claim 48 wherein said oxidant is selected from the group consisting of oxidizing compounds and sulfurizing compounds.

53. A system according to claim 48 wherein said oxidant is an aqueous iodine solution.

* * * * *